United States Patent [19]

Nachbur et al.

[11] 4,185,037

[45] Jan. 22, 1980

[54] PROCESS FOR THE MANUFACTURE OF PHOSPHORUS-CONTAINING CONDENSATION PRODUCTS, THE PRODUCTS AND THEIR USE AS FLAMEPROOFING AGENTS

[75] Inventors: Hermann Nachbur, Dornach; Arthur Maeder, Therwil, both of Switzerland

[73] Assignee: Ciba-Geigy Corporation, Ardsley, N.Y.

[21] Appl. No.: 963,500

[22] Filed: Nov. 24, 1978

Related U.S. Application Data

[63] Continuation of Ser. No. 848,050, Nov. 3, 1977, abandoned, which is a continuation of Ser. No. 584,808, Jun. 9, 1975, abandoned, which is a continuation-in-part of Ser. No. 285,171, Aug. 31, 1972, abandoned.

[51] Int. Cl.$^2$ .................... C07C 87/20; C07C 87/36; C07C 87/52; C07C 91/04
[52] U.S. Cl. ..................... 260/583 E; 260/563 C; 260/578; 260/584 R; 260/584 C; 544/157; 544/402
[58] Field of Search ........... 260/583 E, 584 R, 584 C, 260/578, 579, 583 H

[56] References Cited

U.S. PATENT DOCUMENTS 2,809,941  10/1957  Reeves et al. .............. 260/583 E X

FOREIGN PATENT DOCUMENTS

| | | | |
|---|---|---|---|
| 211637 | 10/1955 | Australia | 260/583 E |
| 269700 | 11/1963 | Australia | 260/583 E |
| 287412 | 7/1964 | Australia | 260/583 E |
| 882993 | 11/1961 | United Kingdom | 260/583 E |
| 935098 | 8/1963 | United Kingdom | 260/583 E |

*Primary Examiner*—John Doll
*Attorney, Agent, or Firm*—Prabodh I. Almaula

[57] ABSTRACT

The subject of the invention is a process for the manufacture of polycondensation products of hydroxymethylphosphonium compounds and an amine, characterized in that (a) 1 mol of a tetrakis-(hydroxymethyl)-phosphonium compound is condensed with 0.02 to 0.3 mol, preferably 0.02 to 0.25 mol, of an amine at 100° to 150° C., optionally in the presence of an inert organic solvent, if appropriate free hydroxyl groups are at least partially etherified with at least one alkanol with 1 to 4 carbon atoms and if appropriate the salts of the polycondensation products are converted into the corresponding hydroxides.

The condensation products are used for flameproofing organic fiber material, especially textiles.

15 Claims, No Drawings

PROCESS FOR THE MANUFACTURE OF PHOSPHORUS-CONTAINING CONDENSATION PRODUCTS, THE PRODUCTS AND THEIR USE AS FLAMEPROOFING AGENTS

This is a continuation of application Ser. No. 848,050 filed on Nov. 3, 1977, (now abandoned); which is a continuation of application Ser. No. 584,808, filed June 9, 1975, (now abandoned), which is a continuation-in-part of application Ser. No. 285,171, filed Aug. 31, 1972, (now abandoned).

The subject of the invention is a process for the manufacture of polycondensation products of hydroxymethylphosphonium compounds and an amine, characterised in that (a) 1 mol of a tetrakis-(hydroxymethyl)-phosphonium compound is condensed with 0.02 to 0.3 mol, preferably 0.02 to 0.25 mol, of an amine at 100° to 150° C., optionally in the presence of an inert organic solvent, if appropriate free hydroxyl groups are at least partially etherified with at least one alkanol with 1 to 4 carbon atoms and if appropriate the salts of the polycondensation products are converted into the corresponding hydroxides.

The condensation is preferably carried out at 110° to 140° C. in an inert organic solvent or solvent mixture. For this, aromatic hydrocarbons are above all suitable, such as, for example, toluene, o-, m- or p-xylene or a mixture thereof, or xylene-toluene, xylene-benzene or xylene-decahydronaphthalene mixtures.

At the same time it is however also possible to carry out the condensation in the absence of an inert organic solvent, for example if polycondensation product already manufactured is used as the solvent or if condensation is carried out in the melt.

An appropriate procedure is to heat the tetrakis(hydroxymethyl)-phosphonium compound, which as a rule is in the form of an aqueous solution, together with the component (b), optionally in a solvent, to the boil, and to distil off the water. This process can be carried out continuously or stepwise, that is to say the mixture can immediately be heated to the requisite temperature or the components (a) and (b) can first be brought together at room temperature, for example 15° to 25° C., and only thereafter be heated to 100°–150° C. Tetrakis-(hydroxymethyl)-phosphonium compounds are above all salts and the hydroxide.

Suitable tetrakis-(hydroxymethyl)-phosphonium salts are, for example, the formate, acetate, phosphate or sulphate and the halides, such as, for example, the bromide or especially the chloride. Tetrakis-(hydroxymethyl)-phosphonium chloride will hereafter be referred to as THPC.

Where tetrakis-(hydroxymethyl)-phosphonium hydroxide (THPOH) is used as the starting product, it is appropriately prepared beforehand from a corresponding salt, for example THPC, by neutralisation in aqueous solution with a base, for example sodium hydroxide, and subsequent dehydration.

More particulary an aliphatic or a 6-membered cycloaliphatic, heterocyclic saturated or aromatic primary amine with at most 8 carbon atoms or a N-hydroxyalkyl or N-alkyl substituted or N-unsubstituted alkylene-diamine with a primary amino group and at most 8 carbon atoms or 0.02 to 0.1 mol of an aliphatic primary amine with 9 to 18 carbon atoms or a polyalkylene-polyamine with 3 to 5 amino groups are used in the process for the manufacture of the condensation products.

As 6-membered cycloaliphatic, primary amines the N- or 2-methylcyclohexylamine and especially the cyclohexylamine are suitable.

As 6-membered heterocyclic saturated, primary amines 1-(2-aminoethyl)-piperazine and above all N-(3-aminopropyl)-morpholine are suitable.

As 6-membered aromatic, primary amines, the toluidines, especially the o-toluidine, and above all the aniline are suitable.

As aliphatic primary amines with at most 8 carbon atoms, the alkyl-, alkenyl-, hydroxyalkyl- and the hydroxyalkoxyalkylamines are preferred.

Examples of alkylamines are the monomethyl- and -ethylamine, the monoiso-1,1-dimethyl- and n-propylamine, the mono-, iso- and s-butylamine, the 3- and 4-aminoheptane, the 1,4-dimethylpentylamine, the n-octylamine, the tertiary octylamine, the mono-2-ethylhexylamine. The most preferred alkylamines are the ethylamine and the tertiary octylamine.

Amongst the alkenylamines allylamine is in particular suitable.

Examples of hydroxyalkylamines are monoethanolamine, monoisopropanolamine, 3-aminopropanol and 3-ethyl-3-aminobutanol-1. The most preferred hydroxyalkylamine is monoethanolamine.

Examples of hydroxyalkoxyalkylamine are 2-methoxyethylamine, 2-ethoxyethylamine, 3-methoxypropylamine, 3-ethoxypropylamine and diglykolamine. The most preferred hydroxyalkoxyalkylamine is diglykolamine.

Examples of N-hydroxyalkyl- or N-alkyl- substituted or N-unsubstituted alkylenediamines with a primary amino group and at most 8 carbon atoms are hydroxyethylethylene-diamine, ethylene-diamine, 2-amino-1-dimethyl-amino-ethane, 2-amino-1-diethyl-amino-ethane, 1,2-propylene-diamine, 1,3-diamino-propane, 3-amino-1-methyl-amino-propane, dimethylamino-propylamine, 1,4-diaminobutane, 4-diethylamino-butylamine, hexamethylene-diamine and 2,5-dimethyl-hexane-2,5-diamine. The most preferred alkylene-diamines are the hydroxyethyl-ethylene-diamine and the ethylene-diamine.

As aliphatic primary amines with 9 to 18 carbon atoms, alkoxyalkylamines such as the 3-(2-ethylhexoxy)-propylamine or above all alkylamines such as the dodecyl-, tridecyl or stearylamine are suitable. The most preferred aliphatic primary amines with 9 to 18 carbon atoms are the dodecyl- and stearylamine.

Examples of polyalkylene-polyamine with 3 to 5 amino groups are the Bis (2-dimethylaminoethyl)-methylamine, diethylene-triamine, dipropylene-triamine, Bis (3-aminopropyl)-methylolamine, 1,2-bis-(3-amino-propylamino)-ethane, tripropylene-tetramine tetraethylene-pentamine and tetrapropylene-pentamine. The most preferred polyalkylene-polyamine are the diethylene-triamine and the tetraethylene-pentamine.

The molar ratio tetrakis-(hydroxymethyl)-phosphonium compound: amine is preferably of 1:0.1 to 0.3 and especially of 1:0.1 to 0.25 for the amines with at most 8 carbon atoms as mentioned above and of 1:0.02 to 0.1 for the amines with 9 to 18 carbon atoms or for the polyalkylene-polyamines with 3 to 5 amino groups as mentioned above.

The etherification of the condensation products still containing free hydroxyl groups, which may have to be carried out, is effected, for example, with n-butanol, n-propanol, ethanol or especially methanol. For this, an acid medium is preferably used.

The acid catalysts optionally used conjointly in the condensation are preferably salts which have an acid action (LEWIS acids), such as magnesium chloride, iron-III chloride, zinc nitrate or boron trifluoride/-diethyl ether. The conjoint use of these catalysts is especially advisable in the condensation of THPOH and when the condensation is carried out at below 120° C.

After completion of the condensation and etherification, if required, the salts of the condensation products can also be completely or partially converted into their corresponding hydroxides, which is as a rule effected by adding strong bases such as alkali metal hydroxides or alkaline earth metal hydroxides, for example sodium hydroxide, potassium hydroxide or calcium hydroxide, or also sodium carbonate. The amount of base is appropriately so chosen that the pH-value of the reaction mixture is about 5 to 8. Appropriately, this conversion is carried out in the bath used for application.

At times, the end products show an unpleasant odour caused by volatile, low molecular trivalent phosphorus compounds, for example phosphines, such as trihydroxymethylphosphine. This odour can be eliminated by an oxidative after-treatment of the condensation product, for example by passing air or oxygen into the reaction mixture or by adding oxidising agents such as, for example, hydrogen peroxide or potassium persulphate.

The condensation products are used for flameproofing organic fibre material, especially textiles. For this, an appropriate procedure is to apply to these materials an aqueous preparation which contains at least (1) a condensation product of the indicated type and (2) a polyfunctional compound which differs from the component (1), and to finish the materials treated in this way by the moist batch, wet batch, above all ammonia or, especially, thermofixing process.

The component (2) is preferably a polyfunctional epoxide or above all a polyfunctional nitrogen compound. Possible epoxides are above all epoxides which are liquid at room temperature and have at least two epoxide groups, which are preferably derived from polyhydric phenols. Polyfunctional nitrogen compounds are, for example, polyalkylenepolyamines or especially compounds which form aminoplasts, or aminoplast precondensates. The latter are preferred.

By compounds which form aminoplasts there are understood nitrogen compounds which can be methylolated and by aminoplast precondensates there are understood addition products of formaldehyde to nitrogen compounds which can be methylolated. As compounds which form aminoplasts or as nitrogen compounds which can be methylolated, there may be mentioned:

1,3,5-aminotriazines such as N-substituted melamines, for example N-butylmelamine, N-trihalogenomethylmelamines, triazones and ammeline, guanamines, for example benzoguanamines and acetoguanamines or also diguanamines.

Further possibilities are: cyanamide, acrylamide, alkylureas or arylureas and alkylthioureas or arylthioureas, alkyleneureas or alkyldiureas, for example, urea, thiourea, urones, ethyleneurea, propyleneurea, acetylenediurea or especially 4,5-dihydroxyimidazolidone-2 and derivatives thereof, for example 4,5-dihydroxyimidazolidone-2 substituted in the 4-position, at the hydroxyl group, by the radical —CH$_2$CH$_2$CO—NH—CH$_2$OH. The methylol compounds of a urea, of an ethyleneurea or, especially, of melamine are preferentially used. Valuable products are in general given by products which are as highly methylolated as possible but in particular also by products with low methylolation. Etherified or non-etherified methylolmelamines are particularly suitable. Suitable aminoplast precondensates are both predominantly monomolecular aminoplasts and also more highly precondensed aminoplasts.

The ethers of these aminoplast precondensates can also be used together with the reaction products. For example, the ethers of alkanols such as methanol, ethanol, n-propanol, isopropanol, n-butanol or pentanols are advantageous. It is, however, desirable, that these aminoplast precondensates should be water-soluble, such as, for example, pentamethylolmelamine-dimethylether.

The organic fibre materials to be provided with a flameproof finish are, for example, wood, paper, furs, hides or, preferably, textiles. In particular, fibre materials of polyamides, cellulose, cellulose-polyester or polyester are flame-proofed, with fabrics of wool or polyester or mixed fabrics of polyester-cellulose, wherein the proportion of polyester to cellulose is 1:4 to 2:1, being preferred. It is thus possible to use, for example, so-called 20/80, 26/74, 50/50 and 67/33 polyester-cellulose mixed fabrics.

The cellulose or the cellulose constituent of the fibre material originates, for example, from linen, cotton, rayon or staple viscose. In addition to polyester-cellulose fibre mixtures it is also possible to use fibre mixtures of cellulose with natural or synthetic polyamides. Above all, fibre materials of wool can also be flameproofed well with the polycondensation products.

The aqueous preparations for flameproofing the organic fibre materials as a rule contain 200 to 600 g/l, preferably 350 to 450 g/l, of the component (1) and 20 to 200 g/l, preferably 40 to b 120 g/l, of the component (2). The preparations in most cases have an acid to neutral or weakly alkaline pH-value, for example 2 to 7.5, preferably 4 to 7.

The preparations for flameproofing can optionally contain yet further additives. To achieve a greater deposit of substance on fabrics it is advantageous, for example, to add 0.1 to 0.5%o of a high molecular polyethylene glycol. Furthermore, the customary plasticisers can be added to the preparations, for example an aqueous polyethylene emulsion or silicone oil emulsion.

To improve the mechanical strengths of the fibres it is also possible to add to the preparations suitable copolymers, for example copolymers of N-methylolacrylamide or cationic copolymers. Advantageous compositions for this purpose are, for example, aqueous emulsions of copolymers of (a) 0.25 to 10% of an alkaline earth metal salt of an α,β-ethylenically unsaturated monocarboxylic acid, (b) 0.25 to 30% of a N-methylolamide or N-methylolamide-ether of an α,β-ethylenically unsaturated monocarboxylic or dicarboxylic acid and (c) 99.5 to 60% of at least one other copolymerisable compound.

These copolymers and their manufacture are known. The tear resistance and abrasion resistance of the treated fibre material can be favourably influenced by the conjoint use of such a copolymer.

If a polymer of the indicated type is also added to the preparation, it is advantageously added in small amounts, for example 1 to 10% relative to the amount of the condensation product. The same is true of any plasticiser which may be added, where the appropriate amounts can again be 1 to 10%.

It is also possible to add curing catalysts, such as, for example, ammonium chloride, ammonium dihydrogen orthophosphate, phosphoric acid, magnesium chloride or zinc nitrate, but is in most cases not necessary.

It can also be advantageous to add buffer substances, for example NaHCO$_3$, disodium and trisodium phosphate or triethanolamine.

To improve the durability of the flameproof finishes and to achieve a soft handle and a low flexural stiffness it can be advantageous to add, to the aqueous preparations, halogenated paraffins in combination with a polyvinyl halide compound.

The preparations are now applied to the fibre materials, which can be done in a manner which is in itself known. Preferably, piece goods are used, and are impregnated on a padder which is fed with the preparation at room temperature.

In the preferred thermofixing process, the fibre material impregnated in this way must now be dried and subjected to a heat treatment. Drying is appropriately carried out at temperatures of up to 100° C. Thereafter the material is subjected to a heat treatment at temperatures above 100° C., for example 100° to 200° C., preferably 120° to 180° C., the duration of which can be the shorter the higher is the temperature. This duration of heating is, for example, 30 seconds to 10 minutes.

If the moist fixing process is used, the fabric is first dried to a residual moisture of about 5 to 20% and is thereafter stored for 12 to 48 hours at about 40° to 60° C., rinsed, washed and dried. In the wet fixing process a similar procedure is followed, except that the completely wet fibre material is stored. In the ammonia fixing process, which next to the thermofixing process is most frequently in the forefront, the treated fibre material is treated with ammonia gas whilst still moist and is subsequently dried.

A rinse with an acid-binding agent, preferably with aqueous sodium carbonate solution, can be appropriate in the case of a strongly acid reaction medium.

In the examples which follow, the percentages and parts are percentages by weight and parts by weight, respectively. The relationship of parts by volume to parts by weight is as of ml to g.

EXAMPLE 1

244 parts of a 78% strength by weight aqueous solution of tetrakis-hydroxymethyl-phosphonium chloride (1 mol) are warmed to 80° C. in a stirred vessel of 500 parts by volume capacity, equipped with a thermometer, water separator and dropping funnel. Thereafter, 9 parts of dodecylamine (0.05 mol) are added over the course of 20 minutes with rapid stirring. After completion of the dropwise addition the mixture is stirred for another 10 minutes, 200 parts of xylene are then added and the whole is warmed to the boil. The azeotropic removal of the water starts at 102° C. In the course of the water being separated off, the internal temperature reaches 134° C. and a total of 71 parts of water are obtained. The condensation product is present as a viscous mass and is dissolved by adding 200 parts of water. The xylene is siphoned off as far as possible and the aqueous solution is again freed of water and residual amounts of xylene in vacuo at 70° C. 162 parts of a yellowish highly viscous product are obtained, which gives a clear solution in water and no precipitate with ammonia.

The infra-red spectrum of this product shows the following bands:

| Broad | band at approx. | 3,240 cm$^{-1}$ | strong |
|---|---|---|---|
| Broad | " | 2,905 cm$^{-1}$ | weak |
| Broad shoulder | " | 2,850 cm$^{-1}$ | weak-medium |
| Broad shoulder | " | 2,650 cm$^{-1}$ | weak-medium |
| Broad shoulder | " | 2,340 cm$^{-1}$ | weak |
| Broad | " | 2,080 cm$^{-1}$ | weak |
| Broad shoulder | " | 1,710 cm$^{-1}$ | weak-medium |
| Broad shoulder | " | 1,660 cm$^{-1}$ | weak-medium |
| Broad | " | 1,640 cm$^{-1}$ | weak-medium |
| Sharp shoulder | " | 1,465 cm$^{-1}$ | weak-medium |
| Sharp shoulder | " | 1,440 cm$^{-1}$ | weak-medium |
| Broad shoulder | " | 1,415 cm$^{-1}$ | weak-medium |
| Sharp shoulder | " | 1,300 cm$^{-1}$ | weak-medium |
| Broad shoulder | " | 1,220 cm$^{-1}$ | weak-medium |
| Broad | " | 1,150 cm$^{-1}$ | weak |
| Broad | " | 1,100 cm$^{-1}$ | weak |
| Broad | " | 1,040 cm$^{-1}$ | weak-medium |
| Sharp shoulder | " | 925 cm$^{-1}$ | weak-medium |
| Broad shoulder | " | 900 cm$^{-1}$ | weak-medium |
| Broad | " | 820 cm$^{-1}$ | weak |
| Broad shoulder | " | 760 cm$^{-1}$ | weak |

EXAMPLE 2

The procedure described in Example 1 is followed but using 18 parts of dodecylamine. A total of 74 parts of water are obtained. After working-up in accordance with Example 1, 145 parts of a yellow, viscous condensation product, which gives a clear solution in water and does not give a precipitate with ammonia are obtained.

The infra-red spectrum of this product shows the following bands:

| Broad | band at approx. | 3,200 cm$^{-1}$ | strong |
|---|---|---|---|
| Broad shoulder | " | 2,900 cm$^{-1}$ | weak |
| Broad shoulder | " | 2,850 cm$^{-1}$ | weak-medium |
| Broad shoulder | " | 2,660 cm$^{-1}$ | weak-medium |
| Broad shoulder | " | 2,500 cm$^{-1}$ | weak |
| Broad shoulder | " | 2,335 cm$^{-1}$ | weak |
| Sharp | " | 2,080 cm$^{-1}$ | weak |
| Broad shoulder | " | 1,705 cm$^{-1}$ | medium |
| Broad shoulder | " | 1,660 cm$^{-1}$ | medium |
| Broad | " | 1,635 cm$^{-1}$ | medium |
| Sharp shoulder | " | 1,460 cm$^{-1}$ | medium |
| Broad | " | 1,415 cm$^{-1}$ | weak-medium |
| Sharp | " | 1,300 cm$^{-1}$ | weak-medium |
| Broad shoulder | " | 1,205 cm$^{-1}$ | weak-medium |
| Broad | " | 1,100 cm$^{-1}$ | weak |
| Broad | " | 1,040 cm$^{-1}$ | medium |
| Sharp shoulder | " | 920 cm$^{-1}$ | weak-medium |
| Broad shoulder | " | 880 cm$^{-1}$ | weak-medium |
| Broad | " | 810 cm$^{-1}$ | weak |
| Broad shoulder | " | 760 cm$^{-1}$ | weak |

EXAMPLE 3

The procedure described in Example 1 is followed, but instead of dodecylamine 14.25 parts of allylamine (0.25 mol) are used. A total of 83 parts of water are obtained. After working-up according to Example 1, 164 parts of a yellow, viscous condensation product are obtained; for greater ease of handling, this is diluted with water to 80% active substance content.

The infra-red spectrum of this product shows the following bands:

| Broad | band at approx. | 3,360 cm$^{-1}$ | strong |
|---|---|---|---|
| Sharp | " | 2,905 cm$^{-1}$ | weak |
| Broad shoulder | " | 2,850 cm$^{-1}$ | weak-medium |
| Broad shoulder | " | 2,650 cm$^{-1}$ | weak-medium |
| Broad shoulder | " | 2,350 cm$^{-1}$ | weak |
| Broad | " | 2,080 cm$^{-1}$ | weak |

| -continued | | | |
|---|---|---|---|
| Sharp shoulder | " | 1,705 cm$^{-1}$ | weak-medium |
| Broad | " | 1,630 cm$^{-1}$ | medium strong |
| Sharp shoulder | " | 1,465 cm$^{-1}$ | weak-medium |
| Broad | " | 1,415 cm$^{-1}$ | medium |
| Sharp | " | 1,300 cm$^{-1}$ | weak |
| Broad shoulder | " | 1,220 cm$^{-1}$ | weak |
| Broad shoulder | " | 1,150 cm$^{-1}$ | medium |
| Sharp | " | 1,095 cm$^{-1}$ | weak |
| Sharp | " | 1,045 cm$^{-1}$ | medium |
| Sharp shoulder | " | 920 cm$^{-1}$ | weak-medium |
| Broad shoulder | " | 890 cm$^{-1}$ | weak |

EXAMPLE 4

The procedure described in Example 1 is followed but instead of the dodecylamine 25.5 parts of 3-dimethylaminopropylamine (0.25 mol) are used.

A total of 76 parts of water is obtained. After working-up in accordance with Example 1, 193 parts of a yellow viscous condensation product are obtained; for greater ease of handling this is diluted with water to 80% active substance content.

The infra-red spectrum of this product shows the following bands:

| Broad | band at approx. | 3,240 cm$^{-1}$ | strong |
|---|---|---|---|
| Sharp | " | 2,910 cm$^{-1}$ | weak |
| Broad shoulder | " | 2,850 cm$^{-1}$ | weak |
| Broad shoulder | " | 2,700 cm$^{-1}$ | weak |
| Broad shoulder | " | 2,480 cm$^{-1}$ | weak |
| Broad shoulder | " | 2,360 cm$^{-1}$ | weak |
| Sharp | " | 2,070 cm$^{-1}$ | weak |
| Broad | " | 1,630 cm$^{-1}$ | medium |
| Broad shoulder | " | 1,470 cm$^{-1}$ | medium |
| Broad | " | 1,410 cm$^{-1}$ | weak-medium |
| Sharp | " | 1,300 cm$^{-1}$ | weak |
| Broad shoulder | " | 1,210 cm$^{-1}$ | weak |
| Broad | " | 1,150 cm$^{-1}$ | weak-medium |
| Sharp | " | 1,100 cm$^{-1}$ | weak |
| Sharp | " | 1,040 cm$^{-1}$ | medium |
| Sharp shoulder | " | 925 cm$^{-1}$ | medium |
| Broad shoulder | " | 890 cm$^{-1}$ | weak-medium |
| Broad shoulder | " | 810 cm$^{-1}$ | weak |

EXAMPLE 5

244 parts (1 mol) of a 78% strength aqueous THPC solution are initially introduced into a stirred vessel of 500 parts by volume capacity, which is equipped with a reflux condenser and thermometer, and are cooled to 5° C. Thereafter 15.2 parts (0.25 mol) of 98.5% strength ethylenediamine are added dropwise over the course of 10 minutes whilst stirring rapidly and cooling with ice, and in the course of the addition the temperature rises to 13° C. Condensation is then allowed to take place for 2 hours at 100°–110° C. After cooling, 255 parts of a clear, yellow solution of low viscosity, containing 76% of active material are obtained.

The infra-red spectrum of this product shows the following bands:

| Broad | band at approx. | 3,240 cm$^{-1}$ | strong |
|---|---|---|---|
| Sharp | " | 2,910 cm$^{-1}$ | weak |
| Broad shoulder | " | 2,850 cm$^{-1}$ | weak |
| Broad shoulder | " | 2,605 cm$^{-1}$ | weak-medium |
| Broad shoulder | " | 2,350 cm$^{-1}$ | weak |
| Broad | " | 2,070 cm$^{-1}$ | weak |
| Broad shoulder | " | 1,705 cm$^{-1}$ | weak |
| Broad | " | 1,630 cm$^{-1}$ | medium |
| Sharp shoulder | " | 1,460 cm$^{-1}$ | medium |
| Broad | " | 1,410 cm$^{-1}$ | medium |

| -continued | | | |
|---|---|---|---|
| Sharp | " | 1,290 cm$^{-1}$ | weak |
| Broad | " | 1,185 cm$^{-1}$ | weak |
| Sharp | " | 1,040 cm$^{-1}$ | strong |
| Broad shoulder | " | 905 cm$^{-1}$ | medium |
| Broad shoulder | " | 875 cm$^{-1}$ | weak-medium |
| Broad shoulder | " | 800 cm$^{-1}$ | weak |

EXAMPLE 6

244 parts (1 mol) of a 78% strength aqueous THPC solution are warmed to 80° C. internal temperature in a stirred vessel of 500 parts by volume capacity which is equipped with a reflux condenser and thermometer. 18 parts (0.1 mol) of dodecylamine are added dropwise over the course of 20 minutes with good stirring and the treatment is continued for 2 hours at 100°–110° C. internal temperature. After cooling, 258 parts of a cloudy solution of low viscosity, containing 80% of active material, is obtained.

The infra-red spectrum of this product shows the following bands:

| Broad | band at approx. | 3,240 cm$^{-1}$ | strong |
|---|---|---|---|
| Sharp | " | 2,920 cm$^{-1}$ | weak |
| Broad shoulder | " | 2,850 cm$^{-1}$ | medium |
| Broad shoulder | " | 2,630 cm$^{-1}$ | medium |
| Broad shoulder | " | 2,460 cm$^{-1}$ | weak |
| Broad shoulder | " | 2,350 cm$^{-1}$ | weak |
| Broad | " | 2,080 cm$^{-1}$ | weak |
| Broad | " | 1,630 cm$^{-1}$ | medium |
| Sharp shoulder | " | 1,460 cm$^{-1}$ | medium |
| Broad | " | 1415 cm$^{-1}$ | medium |
| Sharp | " | 1,300 cm$^{-1}$ | weak |
| Broad shoulder | " | 1,200 cm$^{-1}$ | weak |
| Broad shoulder | " | 1,165 cm$^{-1}$ | weak |
| Broad shoulder | " | 1,105 cm$^{-1}$ | weak |
| Sharp | " | 1,040 cm$^{-1}$ | strong |
| Sharp shoulder | " | 920 cm$^{-1}$ | medium-strong |
| Broad shoulder | " | 880 cm$^{-1}$ | weak-medium |
| Broad shoulder | " | 810 cm$^{-1}$ | weak |

EXAMPLE 7

244 parts (1 mol) of a 78% strength THPC solution are cooled to 5° C. internal temperature in a stirred vessel of 500 parts by volume capacity which is equipped with a water separator, reflux condenser and thermometer, and 15.2 parts (0.25 mol) of 98.5% strength ethylenediamine are then added dropwise over the course of 10 minutes whilst stirring well and cooling with ice. During the addition, the temperature rises to 14° C. 200 parts of xylene isomer mixture are then added and the whole is heated to the boil. The azeotropic removal of the water starts at 100° C. In the course of separating off the water, the internal temperature reaches 132° C. and a total of 81 parts of water are obtained. The condensation product is in the form of a viscous mass and is dissolved by adding 200 parts of water. The xylene is siphoned off as far as possible and the aqueous solution is again freed of water and residual amounts of xylene in vacuo at 70° C. A viscous, yellow, condensation product is obtained, which is diluted with water to 80% active material content to facilitate handling. Yield: 211 parts of 80% strength material.

The infrared spectrum of this product shows the following bands:

| Broad | band at approx. | 3,240 cm$^{-1}$ | strong |
|---|---|---|---|

-continued

| | | | |
|---|---|---|---|
| Sharp | " | 2,905 cm$^{-1}$ | weak |
| Broad shoulder | " | 2,850 cm$^{-1}$ | weak |
| Broad | " | 2,620 cm$^{-1}$ | weak |
| Broad shoulder | " | 2,350 cm$^{-1}$ | weak |
| Sharp shoulder | " | 2,070 cm$^{-1}$ | weak |
| Sharp shoulder | " | 1,710 cm$^{-1}$ | weak-medium |
| Broad | " | 1,630 cm$^{-1}$ | medium |
| Broad shoulder | " | 1,460 cm$^{-1}$ | medium |
| Broad shoulder | " | 1,415 cm$^{-1}$ | medium |
| Sharp | " | 1,295 cm$^{-1}$ | weak |
| Broad shoulder | " | 1,180 cm$^{-1}$ | weak-medium |
| Broad shoulder | " | 1,135 cm$^{-1}$ | weak |
| Broad shoulder | " | 1,100 cm$^{-1}$ | weak |
| Sharp | " | 1,040 cm$^{-1}$ | medium |
| Broad | " | 900 cm$^{-1}$ | weak-medium |

EXAMPLE 8

244 parts (1 mol) of a 78% strength aqueous THPC solution are cooled to 0° C. in a stirred vessel of 500 parts by volume capacity equipped with a reflux condenser and thermometer. 25.5 parts (0.25 mol) of 3-dimethylaminopropylamine are added dropwise over the course of 30 minutes whilst stirring rapidly and cooling with ice, and in the course of the addition the temperature rises to 3° C. Condensation is then allowed to take place for 2 hours at 100°–115° C. After cooling, 262.5 parts of a yellowish solution of low viscosity are obtained. The active material content is 78%.

The infrared spectrum of this product shows the following bands:

| | | | |
|---|---|---|---|
| Broad | band at approx. | 3,240 cm$^{-1}$ | strong |
| Sharp | " | 2,900 cm$^{-1}$ | weak |
| Broad shoulder | " | 2,850 cm$^{-1}$ | weak-medium |
| Broad shoulder | " | 2,630 cm$^{-1}$ | weak-medium |
| Broad shoulder | " | 2,480 cm$^{-1}$ | weak-medium |
| Broad shoulder | " | 2,350 cm$^{-1}$ | weak |
| Sharp | " | 2,070 cm$^{-1}$ | weak |
| Broad shoulder | " | 1,705 cm$^{-1}$ | weak |
| Broad | " | 1,635 cm$^{-1}$ | medium |
| Broad shoulder | " | 1,460 cm$^{-1}$ | medium |
| Broad | " | 1,415 cm$^{-1}$ | medium |
| Sharp | " | 1,300 cm$^{-1}$ | weak |
| Broad | " | 1,190 cm$^{-1}$ | weak |
| Broad | " | 1,140 cm$^{-1}$ | weak |
| Sharp shoulder | " | 1,040 cm$^{-1}$ | medium |
| Broad shoulder | " | 1,015 cm$^{-1}$ | medium |
| Sharp shoulder | " | 920 cm$^{-1}$ | weak-medium |
| Broad shoulder | " | 880 cm$^{-1}$ | weak |
| Broad shoulder | " | 805 cm$^{-1}$ | weak |

EXAMPLE 9

244 parts (1 mol) of a 78% strength aqueous THPC solution are cooled to 10° C. internal temperature in a stirred vessel of 500 parts by volume capacity which is equipped with a water separator, reflux condenser and thermometer, and 21 parts (0.2 mol) of diglycolamine are then added dropwise over the course of 5 minutes whilst stirring well and cooling with ice. In the course of the addition the temperature rises to 16° C. 200 parts of xylene isomer mixture are then added and the whole is heated to the boil. The azeotropic removal of the water starts at 104° C. In the course of separating off the water, the internal temperature reaches 132° C. and the mixture is cooled as soon as 75 parts of water have been separated off. The highly viscous condensation product is dissolved by adding 200 parts of water. The xylene is siphoned off as far as possible and the aqueous solution is again freed of water and residual amounts of xylene in vacuo at 70° C. A viscous condensation product is obtained, which is diluted with water to 80% active material content to facilitate handling. Yield: 225.5 parts of 80% strength material.

The infrared spectrum of this product shows the following bands:

| | | | |
|---|---|---|---|
| Broad | band at approx. | 3,200 cm$^{-1}$ | strong |
| Sharp | " | 2,920 cm$^{-1}$ | weak |
| Broad shoulder | " | 2,850 cm$^{-1}$ | weak-medium |
| Broad shoulder | " | 2,650 cm$^{-1}$ | weak-medium |
| Broad shoulder | " | 2,480 cm$^{-1}$ | weak |
| Broad shoulder | " | 2,350 cm$^{-1}$ | weak |
| Sharp | " | 2,070 cm$^{-1}$ | weak |
| Broad shoulder | " | 1,710 cm$^{-1}$ | weak |
| Broad | " | 1,635 cm$^{-1}$ | medium |
| Sharp shoulder | " | 1,465 cm$^{-1}$ | weak-medium |
| Broad | " | 1,415 cm$^{-1}$ | medium |
| Sharp | " | 1,300 cm$^{-1}$ | weak |
| Broad shoulder | " | 1,200 cm$^{-1}$ | weak |
| Broad shoulder | " | 1,160 cm$^{-1}$ | weak |
| Broad shoulder | 41 | 1,130 cm$^{-1}$ | weak |
| Broad | " | 1,100 cm$^{-1}$ | weak |
| Sharp | " | 1,045 cm$^{-1}$ | medium-weak |
| Sharp shoulder | " | 920 cm$^{-1}$ | medium |
| Broad shoulder | " | 890 cm$^{-1}$ | weak-medium |
| Broad shoulder | " | 815 cm$^{-1}$ | weak |

EXAMPLE 10

244 parts (1 mol) of a 78% strength aqueous THPC solution are cooled to 0° C. in a stirred vessel of 500 parts by volume capacity which is equipped with a reflux condenser and thermometer. 15.25 parts (0.25 mol) of monoethanolamine are added dropwise over the course of 20 minutes whilst stirring rapidly and cooling with ice; during the course of the addition the temperature rises to 3° C. Thereafter, condensation is allowed to take place for 2 hours at 100°–105° C. After cooling, 255 parts of a yellowish solution of low viscosity are obtained. The active material content is 80.5%.

The infrared spectrum shows the following bands:

| | | | |
|---|---|---|---|
| Broad | band at approx. | 3,240 cm$^{-1}$ | strong |
| Sharp | " | 2,920 cm$^{-1}$ | weak |
| Broad shoulder | " | 2,850 cm$^{-1}$ | weak-medium |
| Broad shoulder | " | 2,630 cm$^{-1}$ | weak-medium |
| Broad shoulder | " | 2,350 cm$^{-1}$ | weak |
| Broad | " | 2,070 cm$^{-1}$ | weak |
| Broad shoulder | " | 1,700 cm$^{-1}$ | weak |
| Broad | " | 1,630 cm$^{-1}$ | medium |
| Sharp shoulder | " | 1,460 cm$^{-1}$ | weak-medium |
| Broad | " | 1,410 cm$^{-1}$ | medium |
| Sharp | " | 1,290 cm$^{-1}$ | weak |
| Broad shoulder | " | 1,180 cm$^{-1}$ | weak |
| Broad shoulder | " | 1,160 cm$^{-1}$ | weak |
| Sharp | " | 1,040 cm$^{-1}$ | strong |
| Broad shoulder | " | 910 cm$^{-1}$ | medium |
| Broad | " | 870 cm$^{-1}$ | medium |
| Broad shoulder | " | 810 cm$^{-1}$ | weak |

EXAMPLE 11

244 parts (1 mol) of a 78% strength aqueous THPC solution are cooled to 0° C. in a stirred vessel of 500 parts by volume capacity which is equipped with a reflux condenser and thermometer. 18.6 parts (0.2 mol) of aniline are added dropwise over the course of 5 minutes whilst stirring rapidly and cooling with ice; in the course of the addition, the temperature rises to 5° C. Thereafter condensation is allowed to take place for 2 hours at 100°–110° C. After cooling, 259 parts of a red solution of low viscosity are obtained. The active material content is 75.8%.

The infrared spectrum shows the following bands:

| Broad | band at approx. | 3,200 cm$^{-1}$ | strong |
|---|---|---|---|
| Sharp | " | 2,905 cm$^{-1}$ | weak |
| Broad shoulder | " | 2,850 cm$^{-1}$ | weak-medium |
| Broad shoulder | " | 2,620 cm$^{-1}$ | weak-medium |
| Broad shoulder | " | 2,460 cm$^{-1}$ | weak |
| Broad shoulder | " | 2,350 cm$^{-1}$ | weak |
| Sharp | " | 2,070 cm$^{-1}$ | weak-medium |
| Broad shoulder | " | 1,710 cm$^{-1}$ | weak-medium |
| Broad | " | 1,630 cm$^{-1}$ | medium |
| Sharp | " | 1,500 cm$^{-1}$ | weak-medium |
| Sharp Shoulder | " | 1,460 cm$^{-1}$ | weak |
| Broad | " | 1,405 cm$^{-1}$ | weak-medium |
| Sharp | " | 1,295 cm$^{-1}$ | weak |
| Broad shoulder | " | 1,185 cm$^{-1}$ | weak |
| Broad shoulder | " | 1,130 cm$^{-1}$ | weak |
| Broad | " | 1,035 cm$^{-1}$ | medium |
| Sharp shoulder | " | 910 cm$^{-1}$ | medium |
| Broad shoulder | " | 875 cm$^{-1}$ | weak |
| Broad shoulder | " | 815 cm$^{-1}$ | weak |

EXAMPLE 12

244 parts (1 mol) of a 78% strength aqueous THPC solution are cooled to 0° C. in a stirred vessel of 500 parts by volume capacity which is equipped with a reflux condenser and thermometer. 11.2 parts (0.1 mol) of 92.1% strength diethylenetriamine are added dropwise over the course of 10 minutes whilst stirring rapidly and cooling with ice; in the course of the addition, the temperature rises to 9° C. Condensation is then allowed to take place for 2 hours at 100°–115° C. After cooling, 251.5 parts of a yellow liquid of low viscosity are obtained. The active material content is 80.2%.

The infrared spectrum shows the following bands:

| Broad | band at approx. | 3,240 cm$^{-1}$ | strong |
|---|---|---|---|
| Sharp | " | 2,905 cm$^{-1}$ | weak |
| Broad shoulder | " | 2,850 cm$^{-1}$ | weak-medium |
| Broad shoulder | " | 2,610 cm$^{-1}$ | weak-medium |
| Broad shoulder | " | 2,480 cm$^{-1}$ | weak |
| Broad shoulder | " | 2,350 cm$^{-1}$ | weak-medium |
| Sharp | " | 2,070 cm$^{-1}$ | weak-medium |
| Broad shoulder | " | 1,700 cm$^{-1}$ | medium |
| Broad | " | 1,635 cm$^{-1}$ | medium |
| Sharp shoulder | " | 1,460 cm$^{-1}$ | medium |
| Broad | " | 1,410 cm$^{-1}$ | weak-medium |
| Sharp | " | 1,290 cm$^{-1}$ | weak |
| Broad shoulder | " | 1,185 cm$^{-1}$ | weak |
| Broad shoulder | " | 1,130 cm$^{-1}$ | weak |
| Broad | " | 1,040 cm$^{-1}$ | medium |
| Sharp shoulder | " | 915 cm$^{-1}$ | medium |
| Broad shoulder | " | 880 cm$^{-1}$ | weak-medium |
| Broad shoulder | " | 810 cm$^{-1}$ | weak |

EXAMPLE 13

244 parts (1 mol) of a 78% strength aqueous THPC solution are cooled to −8° C. in a stirred vessel of 500 parts by volume capacity which is equipped with a reflux condenser and thermometer. 9.45 parts (0.05 mol) of tetraethylenepentamine are added dropwise over the course of 6 minutes whilst stirring rapidly and cooling with ice; in the course of the addition, the temperature rises to +1° C. Condensation is then allowed to take place for 2 hours at 100°–110° C. After cooling, 249 parts of a red-yellow liquid of low viscosity are obtained. The active material content is 81.4%.

The infrared spectrum shows the following bands:

| Broad | band at approx. | 3,240 cm$^{-1}$ | strong |
|---|---|---|---|
| Sharp | " | 2,920 cm$^{-1}$ | weak |
| Broad shoulder | " | 2,850 cm$^{-1}$ | medium |
| Broad shoulder | " | 2,630 cm$^{-1}$ | medium |
| Broad shoulder | " | 2,480 cm$^{-1}$ | weak |
| Broad shoulder | " | 2,350 cm$^{-1}$ | weak |
| Sharp | " | 2,070 cm$^{-1}$ | weak |
| Broad shoulder | " | 1,700 cm$^{-1}$ | weak |
| Broad | " | 1,630 cm$^{-1}$ | medium |
| Sharp shoulder | " | 1,460 cm$^{-1}$ | medium |
| Broad | " | 1,410 cm$^{-1}$ | medium |
| Sharp | " | 1,300 cm$^{-1}$ | weak |
| Broad | " | 1,190 cm$^{-1}$ | weak |
| Broad shoulder | " | 1,125 cm$^{-1}$ | weak |
| Broad | " | 1,040 cm$^{-1}$ | strong |
| Sharp shoulder | " | 920 cm$^{-1}$ | medium |
| Broad shoulder | " | 880 cm$^{-1}$ | weak-medium |
| Broad shoulder | " | 810 cm$^{-1}$ | weak |

EXAMPLE 14

244 parts (1 mol) of a 78% strength aqueous THPC solution are cooled to 0° C. in a stirred vessel of 500 parts by volume capacity which is equipped with a reflux condenser and thermometer. 14.4 parts (0.1 mol) of N-(3-aminopropyl)morpholine are added dropwise over the course of 8 minutes whilst stirring rapidly and cooling with ice; in the course of the addition, the temperature rises to 4° C. Hereafter condensation is allowed to take place for 2 hours at 110°–112° C. After cooling, 253.5 parts of a yellow liquid of low viscosity are obtained. The active material content is 81.8%.

The infrared spectrum shows the following bands:

| Broad | band at approx. | 3,240 cm$^{-1}$ | strong |
|---|---|---|---|
| Sharp | " | 2,920 cm$^{-1}$ | weak |
| Broad shoulder | " | 2,850 cm$^{-1}$ | weak-medium |
| Broad shoulder | " | 2,640 cm$^{-1}$ | weak-medium |
| Broad shoulder | " | 2,480 cm$^{-1}$ | weak |
| Broad shoulder | " | 2,350 cm$^{-1}$ | weak |
| Sharp | " | 2,070 cm$^{-1}$ | weak |
| Broad shoulder | " | 1,700 cm$^{-1}$ | weak |
| Broad | " | 1,630 cm$^{-1}$ | medium |
| Sharp shoulder | " | 1,465 cm$^{-1}$ | medium |
| Broad | " | 1,410 cm$^{-1}$ | medium |
| Sharp | " | 1,300 cm$^{-1}$ | weak |
| Broad | " | 1,190 cm$^{-1}$ | weak |
| Broad shoulder | " | 1,120 cm$^{-1}$ | weak |
| Broad | " | 1,040 cm$^{-1}$ | strong |
| Sharp shoulder | " | 920 cm$^{-1}$ | medium |
| Broad shoulder | " | 880 cm$^{-1}$ | weak-medium |
| Broad shoulder | " | 810 cm$^{-1}$ | weak |

EXAMPLE 15

244 parts (1 mol) of a 78% strength aqueous THPC solution are cooled to 0° C. in a stirred vessel of 500 parts by volume capacity which is equipped with a reflux condenser and thermometer. 20.8 parts (0.2 mol) of hydroxyethylethylenediamine are added dropwise over the course of 13 minutes whilst stirring rapidly and cooling with ice; in the course of the addition, the temperature rises to 8° C. Thereafter condensation is allowed to take place for 2 hours at 105°–115° C. After cooling, 258 parts of a yellow liquid of low viscosity are obtained. The active material content is 76%.

The infrared spectrum shows the following bands:

| Broad | band at approx. | 3,240 cm$^{-1}$ | strong |
|---|---|---|---|
| Sharp | " | 2,920 cm$^{-1}$ | weak |
| Broad shoulder | " | 2,850 cm$^{-1}$ | weak-medium |

-continued

| | | | |
|---|---|---|---|
| Broad shoulder | " | 2,630 cm$^{-1}$ | weak |
| Broad shoulder | " | 2,480 cm$^{-1}$ | weak |
| Broad shoulder | " | 2,350 cm$^{-1}$ | weak |
| Broad | " | 2,070 cm$^{-1}$ | weak |
| Broad shoulder | " | 1,710 cm$^{-1}$ | weak |
| Broad | " | 1,630 cm$^{-1}$ | medium |
| Sharp shoulder | " | 1,465 cm$^{-1}$ | medium |
| Broad | " | 1,410 cm$^{-1}$ | medium |
| Sharp | " | 1,300 cm$^{-1}$ | weak |
| Broad | " | 1,190 cm$^{-1}$ | weak |
| Broad shoulder | " | 1,120 cm$^{-1}$ | weak |
| Sharp | " | 1,040 cm$^{-1}$ | strong |
| Sharp shoulder | " | 915 cm$^{-1}$ | medium |
| Broad shoulder | " | 880 cm$^{-1}$ | weak-medium |
| Broad shoulder | " | 800 cm$^{-1}$ | weak |

EXAMPLE 16

244 parts (1 mol) of a 78% strength aqueous THPC solution are cooled to 6° C. in a stirred vessel of 500 parts by volume capacity which is equipped with a reflux condenser and thermometer. 52.5 parts (0.5 mol) of diglycolamine are added dropwise over the course of 5 minutes whilst stirring vigorously and cooling with ice; in the course of the addition, the temperature rises to 17° C. Thereafter condensation is allowed to take place for 2 hours at 105°–110° C. After cooling, 293 parts of a yellow solution of low viscosity are obtained. The active material content is 76%.

The infrared spectrum shows the following bands:

| | | | |
|---|---|---|---|
| Broad | band at approx. | 3,240 cm$^{-1}$ | strong |
| Sharp | " | 2,905 cm$^{-1}$ | weak |
| Broad shoulder | " | 2,850 cm$^{-1}$ | weak |
| Broad shoulder | " | 2,630 cm$^{-1}$ | weak |
| Broad shoulder | " | 2,470 cm$^{-1}$ | weak |
| Broad shoulder | " | 2,350 cm$^{-1}$ | weak |
| Broad | " | 2,060 cm$^{-1}$ | weak |
| Broad shoulder | " | 1,700 cm$^{-1}$ | weak |
| Broad | " | 1,640 cm$^{-1}$ | medium |
| Sharp shoulder | " | 1,460 cm$^{-1}$ | medium |
| Broad | " | 1,410 cm$^{-1}$ | medium |
| Sharp | " | 1,295 cm$^{-1}$ | weak |
| Broad shoulder | " | 1,210 cm$^{-1}$ | weak |
| Broad shoulder | " | 1,180 cm$^{-1}$ | weak |
| Sharp | " | 1,120 cm$^{-1}$ | weak |
| Sharp | " | 1,040 cm$^{-1}$ | strong |
| Sharp | " | 915 cm$^{-1}$ | medium |
| Broad | " | 880 cm$^{-1}$ | weak-medium |
| Broad shoulder | " | 805 cm$^{-1}$ | weak |

EXAMPLE 17

244 parts (1 mol) of a 78% strength aqueous THPC solution are cooled to 10° C. in a stirred vessel of 500 parts by volume capacity which has been equipped with a reflux condenser and thermometer, and are neutralised to pH 7.2 with 56.2 parts of 30% strength aqueous sodium hydroxide solution whilst stirring rapidly and cooling with ice. Thereafter 16.1 parts (0.25 mol) of a 70% strength aqueous ethylamine solution are added dropwise over the course of 5 minutes under the same conditions; during the addition, the temperature rises to 18° C. Condensation is then allowed to take place for 2 hours at 100°–105° C. After cooling, 311 parts of a colourless solution of low viscosity are obtained. The phosphorus content is 9.9% calculated relative to the product as obtained.

The infrared spectrum of this product shows the following bands:

| | | | |
|---|---|---|---|
| Broad | band at approx. | 3,240 cm$^{-1}$ | strong |
| Sharp | " | 2,905 cm$^{-1}$ | weak |
| Broad shoulder | " | 2,850 cm$^{-1}$ | weak-medium |
| Broad shoulder | " | 2,630 cm$^{-1}$ | weak-medium |
| Broad shoulder | " | 2,490 cm$^{-1}$ | weak |
| Broad shoulder | " | 2,350 cm$^{-1}$ | weak |
| Broad | " | 2,070 cm$^{-1}$ | weak |
| Broad shoulder | " | 1,690 cm$^{-1}$ | weak |
| Broad shoulder | " | 1,630 cm$^{-1}$ | medium |
| Broad shoulder | " | 1,590 cm$^{-1}$ | weak |
| Sharp shoulder | " | 1,460 cm$^{-1}$ | medium |
| Broad | " | 1,410 cm$^{-1}$ | medium |
| Sharp | " | 1,295 cm$^{-1}$ | weak |
| Broad shoulder | " | 1,195 cm$^{-1}$ | weak |
| Broad | " | 1,125 cm$^{-1}$ | weak |
| Sharp shoulder | " | 1,040 cm$^{-1}$ | medium |
| Broad shoulder | " | 1,010 cm$^{-1}$ | medium-strong |
| Sharp shoulder | " | 915 cm$^{-1}$ | weak-medium |
| Broad | " | 870 cm$^{-1}$ | weak-medium |
| Broad shoulder | " | 810 cm$^{-1}$ | weak |

EXAMPLE 18

180 parts (0.945 mol) of anhydrous crystalline THPC and 5.09 parts (0.0189 mol) of stearylamine are condensed for 2 hours in the melt, at 105°–115° C., in a stirred vessel of 500 parts by volume capacity which is equipped with a reflux condenser and thermometer. Thereafter the mixture is cooled to 50° C. internal temperature, 80 parts of methanol and 0.1 part of 37% strength aqueous HCl are added and etherification is carried out for 30° at the reflux temperature (63°–64° C.). After cooling to 50° C., the excess methanol is removed in vacuo. 181 parts of a pasty condensate, which dissolves in warm water to give an opalescent solution, are obtained.

The infrared spectrum shows the following bands:

| | | | |
|---|---|---|---|
| Broad | band at approx. | 3,340 cm$^{-1}$ | strong |
| Sharp | " | 2,920 cm$^{-1}$ | weak |
| Broad shoulder | " | 2,850 cm$^{-1}$ | medium |
| Broad shoulder | " | 2,640 cm$^{-1}$ | weak-medium |
| Broad shoulder | " | 2,480 cm$^{-1}$ | weak |
| Broad shoulder | " | 2,360 cm$^{-1}$ | weak |
| Broad | " | 2,060 cm$^{-1}$ | weak |
| Broad | " | 1,620 cm$^{-1}$ | medium |
| Sharp shoulder | " | 1,460 cm$^{-1}$ | weak-medium |
| Broad | " | 1,410 cm$^{-1}$ | medium |
| Sharp | " | 1,290 cm$^{-1}$ | weak |
| Broad | " | 1,190 cm$^{-1}$ | weak-medium |
| Broad shoulder | " | 1,160 cm$^{-1}$ | weak |
| Sharp | " | 1,035 cm$^{-1}$ | strong |
| Broad shoulder | " | 905 cm$^{-1}$ | medium |
| Broad shoulder | " | 875 cm$^{-1}$ | medium |
| Broad shoulder | " | 815 cm$^{-1}$ | weak |

EXAMPLE 19

244 parts (1 mol) of a 78% strength aqueous THPC solution are cooled to 6° C. internal temperature in a stirred vessel of 500 parts by volume capacity which is equipped with a reflux condenser and thermometer. 21 parts (0.2 mol) of diglycolamine are added dropwise over the course of 5 minutes whilst stirring rapidly and cooling with ice; in the course of the addition, the temperature rises to 10° C. Thereafter, condensation is allowed to take place for 2 hours at 105°–110° C. internal temperature. After cooling, 262 parts of a yellow liquid of low viscosity are obtained. The phosphorus content is 11.8% calculated relative to the product as obtained.

The infrared spectrum shows the following bands:

| | | | |
|---|---|---|---|
| Broad | band at approx. | 3,240 cm$^{-1}$ | strong |
| Broad | " | 2,900 cm$^{-1}$ | weak |
| Broad shoulder | " | 2,850 cm$^{-1}$ | weak-medium |
| Broad shoulder | " | 2,630 cm$^{-1}$ | weak-medium |
| Broad shoulder | " | 2,480 cm$^{-1}$ | weak |
| Broad shoulder | " | 2,360 cm$^{-1}$ | weak |
| Sharp | " | 2,080 cm$^{-1}$ | weak-medium |
| Broad shoulder | " | 1,710 cm$^{-1}$ | weak-medium |
| Broad | " | 1,640 cm$^{-1}$ | medium |
| Sharp shoulder | " | 1,460 cm$^{-1}$ | medium |
| Broad | " | 1,410 cm$^{-1}$ | medium |
| Sharp | " | 1,295 cm$^{-1}$ | weak |
| Broad | " | 1,190 cm$^{-1}$ | weak |
| Broad | " | 1,120 cm$^{-1}$ | weak |
| Broad | " | 1,035 cm$^{-1}$ | medium |
| Sharp shoulder | " | 915 cm$^{-1}$ | weak-medium |
| Broad shoulder | " | 880 cm$^{-1}$ | weak-medium |
| Broad shoulder | " | 810 cm$^{-1}$ | weak |

EXAMPLE 20

244 parts (1 mol) of an aqueous solution of THPC (78%) are heated to 80° C. 38.7 parts (0.3 mol) of tertiary octyl amine (100%) are added thereto over the course of 35 minutes. The reaction mixture is kept for 2 hours at 100° to 110° C. After cooling the reaction mixture, 283 parts of a clear, yellow solution of low viscosity containing 77% of the condensation product are obtained.

EXAMPLE 21

244 parts (1 mol) of an aqueous solution of THPC (78%) are neutralized at 10° C. to pH 7.2 with 78.1 parts of an aqueous sodium hydroxide solution (30%) 21.2 parts (0.3 mol) of an aqueous ethylamine solution (70.6%) are added to the reaction mixture over the course of 25 minutes, whereby the temperature rises to 15° C. The reaction mixture is heated to 100 to 105° C. and the condensation reaction is carried out at 100° to 105° C. for 2 hours. After cooling of the reaction mixture, 341 parts of a colourless, viscous solution containing 48.8% of the condensation product are obtained.

EXAMPLE 22

244 parts (1 mol) of an aqueous solution of THPC (78%) are warmed to 80° C. 17.5 parts (0.3 mol) of allylamine (98%) are added to the reaction mixture over the course of 25 minutes. Thereafter 200 parts of xylene are added and the reaction mixture is then heated to the boil. The azeotropic removal of the water starts at 100° C. The temperature of the reaction mixtures reaches 133° C. in the course of the water being separated off, whereby a total of 84 parts of water are obtained. The condensation product is a viscous mass and is dissolved by adding 200 parts of water. The xylene is siphoned off and the aqueous solution is freed of water and residual amounts of xylene is vacuo at 70° C. 171 parts of a clear, water-soluble yellowish viscous product are obtained which. For a better handling, the product was dissolved in water to obtain a solution containing 80% of the condensation product.

EXAMPLE 23

Mixed fabrics of polyester/cotton (PES/CO) (67/33) are padded with the liquors according to the following Table 1, dried at 80° to 100° C. and subsequently cured for 5 minutes at 150° C.

The fabric is then washed for 5 minutes at 60° C. in a liquor which contains, per litre, 5 ml of hydrogen peroxide (35% strength), 3 g of sodium hydroxide solution (30% strength) and 1 g of a 25% strength aqueous solution of a condensation product of 1 mol of p-tert.-nonylphenol and 9 mols of ethylene oxide. Thereafter the fabric is rinsed and dried. The degree of fixing indicates the amount of product present on the fibre after the post-washing treatment (relative to the amount originally absorbed).

The fabrics are then washed up to 40 times for 45 minutes at 60° C. in a domestic washing machine, in a liquor which contains 4 g/l of a domestic detergent (SNV 158.861 wash).

The individual fabric samples are then tested for their flameproof character (DIN 53,906 vertical test; ignition time 6 seconds).

The results are summarised in Table 1 which follows.

Table 1

| | | Treated with liquor | | | |
|---|---|---|---|---|---|
| Constituents (g/l) | Untreated | A | B | C | D |
| Product according to Example 1 | 550 | — | — | — | |
| Product according to Example 2 | — | 550 | — | — | |
| Product according to Example 3 | — | — | 690 | — | |
| Product according to Example 4 | — | — | — | 485 | |
| Dimethylolmelamine | | 96.5 | 96.5 | 96.5 | 96.5 |
| pH value of the liquor (adjusted with NaOH) | | 5.5 | 5.5 | 5.5 | 5.5 |
| Liquor uptake (%) | | 75 | 75 | 75 | 75 |
| Degree of fixing (%) | | 65 | 69 | 81 | 65 |
| Flameproof character | Smouldering time (seconds)/ Tear length (cm) | | | | |
| After rinsing | burns | 0/12.5 | 0/11 | 0/11 | 0/8.5 |
| After 20 washes (60° C.) | burns | 0/9.5 | 0/9.5 | 0/8 | 0/7.5 |
| After 40 washes (60° C.) | burns | 12/8 | 6/9.5 | 4/9 | 14/9.5 |

EXAMPLE 24

Mixed fabrics of polyester-cotton (PES/CO), 50:50, and fabrics of wool (W) are padded with the liquors according to the following Table 2, dried at 80° to 100° C. and subsequently cured for 5 minutes at 150° C.

The fabrics are subsequently washed as indicated in Example 20 (W 40° C., PES/CO 60° C.), rinsed and dried.

The fabrics are then washed up to 20 times for 45 minutes at 60° C. (W 40° C.) in a domestic washing machine in a liquor which contains 4 g/l of a domestic detergent (SNV 198,861 wash). The individual fabric samples are then tested for their flameproof character (DIN 53,906 vertical test; ignition time 6 seconds). Untreated fabrics burn away.

The results are summarised in the following Table 2.

Table 2

| Constituents g/l | Treated with | | | | | | | | | | |
|---|---|---|---|---|---|---|---|---|---|---|---|
| | PES/CO 50:50 | | | | | PES/CO 67:33 | | | | | W |
| | A | B | C | D | E | F | G | H | I | J | K |
| Product according to Example | | | | | | | | | | | |
| 5 | | | | | | 674 | | | | | |
| 6 | 680 | | | | | | | | | | |
| 8 | | 691 | | | | | 691 | | | | |
| 9 | | | | | | | | | 468 | | |
| 11 | | | 680 | | | | | 680 | | | |
| 15 | | | | 680 | | | | | | | |
| 16 | | | | | 775 | | | | 775 | | |
| 17 | | | | | | | | | | | 680 |
| Di-Trimethylolmelamine | 103 | 103 | 103 | 103 | | 103 | 103 | 103 | | 96.5 | 84.5 |
| Trimethylolmelamine-dimethyl-ether (75% strength) | | | | | 153 | | | | 153 | | |
| Condensation product* | | | | | | | | | | | 2 |
| Silicone oil emulsion (40%) | 35 | 35 | 35 | 35 | 35 | 35 | 35 | 35 | 35 | — | 35 |
| pH value of the bath | 5.5 | 5.5 | 5.5 | 5.5 | 5.5 | 5.5 | 5.5 | 5.5 | 6.5 | 5.5 | 7 |
| Degree of fixing, % | 54 | 52 | 60 | 53 | 67 | 55 | 78 | 84 | 70 | 81 | 43 |
| Flameproof character: burning time (seconds) / Tear length (cm) | | | | | | | | | | | |
| After rinsing | 0/7.5 | 0/9 | 0/8 | 0/7.5 | 0/9 | 0/11.5 | 0/12.5 | 0/12 | 0/10 | 0/11 | 0/8 |
| After 1 wash | 0/9 | 0/11 | 0/9 | 4/11 | 0/10 | 6/11.5 | 2/10 | 0/12 | 0/11 | — | 4/4 |
| After 5 washes | 0/7 | 0/11 | 2/9 | 3/8 | 0/8 | 8/12 | 3/10 | 0/11 | 0/12 | 0/9.5⊕ | 4/9 |
| After 20 washes | 0/5.5 | 1/11 | 0/8 | 3/8 | 0/8 | 14/13 | 6/10 | 3/10 | 0/13 | 0/10.5++ | 4/8 |

*from 1 mol of p-tert.-monylphenol and 9 mol of ethylene oxide.
⊕ After 20 washes
++ After 40 washes

EXAMPLE 25

Mixed fabrics of polyester/cotton, PES/CO 50:50, are padded with the liquors according to the following Table 3, dried at 80° to 100° C. and subsequently cured for 5 minutes at 150° C.

The fabrics are subsequently washed as indicated in Example 20 (W 40°, PES/CO 60° C.), rinsed and dried.

The fabrics are then washed up to 5 times for 45 minutes at 60° C. in a domestic washing machine in a liquor which contains 4 g/l of a domestic detergent (SNV 198,861 wash). The individual fabric samples are then tested for their flameproof character (DIN 53,906 vertical test; ignition time 6 seconds). Untreated fabrics burn away.

The results are summarised in Table 3 below.

Table 3

| Constituents g/l | Treated with | | | | | | |
|---|---|---|---|---|---|---|---|
| | A | B | C | D | E | F | G |
| Product according to Example | | | | | | | |
| 5 | 674 | | | | | | |
| 10 | | 674 | | | | | |
| 12 | | | 664 | | | | |
| 13 | | | | 658 | | | |
| 16 | | | | | 775 | | |
| 17 | | | | | | 825 | |
| 18 | | | | | | | 460 |
| Di-Trimethylol-melamine | 103 | 103 | 103 | 103 | | 103 | 103 |
| Trimethylol-melamine-dimethyl-ether (75% strength) | | | | | 153 | | |
| Silicone oil emulsion (40%) | 35 | 35 | 35 | 35 | 35 | | 35 |
| pH of the liquor | 5.5 | 5.5 | 5.5 | 5.5 | 4.5 | 7⊕ | 5.5 |
| Degree of fixing | 55 | 55 | 54 | 53 | 70 | 57 | 43 |
| Flameproof character: burning time (seconds) / Tear length (cm) | | | | | | | |
| After rinsing | 0/7 | 0/5.5 | 0/7.5 | 0/7 | 0/10 | 0/10.5 | 3/11 |
| After 1 wash | 0/9 | 0/9.5 | 0/8 | 0/9.5 | 0/8 | 0/9 | 0/9.5 |
| After 5 washes | 0/10 | 1/9 | 0/11 | 6/10 | 0/12 | 7/13.5 | 0/9 |

⊕Product converted into hydroxyl compound.

EXAMPLE 26

Mixed fabrics of polyester/cotton, PES/CO 67:33 and 50:50, are padded with the liquors of Table 4 below and then treated by the ammonia fixing process as follows:

The padded fabric is incompletely dried at up to 80° C., treated for 10 minutes with ammonia gas, then padded in a liquor which contains 300 ml of a 24% strength aqueous ammonia solution per litre, and immediately thereafter rinsed at 40° C. in a bath which contains 5 g/l of soap and 6 ml of hydrogen peroxide (35% strength), and then dried.

The fabrics are then washed at 60° C. as indicated in Example 24 and thereafter tested according to DIN 53,906 (ignition time 6 seconds) for their flameproof character. Untreated fabrics burn away.

The results are summarised in Table 4 below.

Table 4

| Constituents, g/l | Treated with | |
|---|---|---|
| | PES/CO 50:50 | PES/CO 67:33 |
| | A | B |
| Product according to Example 17, g/l | 460 | |
| Product according to Example 19, g/l | | 460 |
| Di-trimethylolmelamine | 103 | 103 |
| Silicone oil emulsion (40% strength) | 35 | 35 |
| pH value of the liquor | 5.5 | 5.5 |
| Flameproof character | | |
| After rinsing: | | |
| Burning time (seconds) | 0 | 0 |
| Tear length (cm) | 7.5 | 7.5 |
| + After 1 wash: | | |
| Burning time (seconds) | 0 | 0 |
| Tear length (cm) | 9 | 11.5 |

EXAMPLE 27

Mixed fabrics of polyester/cotton, PES/CO 67:33 and 50:50 are padded with the liquors according to the following Table 5, dried at 80° to 100° C. and subsequently cured for 5 minutes at 150° C.

The fabrics are subsequently rinsed as indicated in Example 21 (W 40° C., PES/CO 60° C.) and dried.

The fabrics are then washed at 60° C. as indicated in Example 25 and thereafter tested for their flameproof character according to DIN 53,906 (ignition time 6 seconds). Untreated fabrics burn away.

The results are summarised in Table 5 below.

Table 5

| Constituents g/l | Treated with | | | | | | |
|---|---|---|---|---|---|---|---|
| | PES/CO 50:50 | | PES/CO 67:33 | | | | |
| | A | B | C | D | E | F | G |
| Product according to Example | | | | | | | |
| 10 | 674 | | | | | | |
| 13 | | 658 | | | | | |
| 14 | | | 665 | | | | |
| 15 | | | | 680 | | | |
| 16 | | | | | 775 | | |
| 17 | | | | | | 825 | |
| 19 | | | | | | | 690 |
| Di-Trimethylol-melamine | 103 | 103 | 103 | 103 | | 103 | 103 |
| Trimethylolmelaminedi-methylether (75% strength) | 35 | 35 | 35 | | 35 | 35 | 35 |
| pH value of the bath | 5.5 | 5.5 | 5.5 | 5.5 | 4.5 | 7⊕ | 4.5 |
| Degree of fixing % | 70 | 56 | 56 | 82 | 74 | 66 | 89 |

Flameproof character: burning time (seconds) / Tear length (cm)
After rinsing   0/9   0/13   0/7.5   0/10   0/13   2/10   0/9

Table 5-continued

| Constituents g/l | Treated with | | | | | | |
|---|---|---|---|---|---|---|---|
| | PES/CO 50:50 | | PES/CO 67:33 | | | | |
| | A | B | C | D | E | F | G |
| After washing | 2/10.5 | 0/11.5 | 3/8.5 | 0/6.5 | 0/10.5 | 0/11 | 0/10 |

⊕Product converted into hydroxyl compound.

Trimethylolmelaminedi- | | | | | 153 | | |

EXAMPLE 28

Mixed fabrics of CO, PES/CO 50:50 and 67:33 are padded with the liquors according to the following Table 6, dried at 80° to 100° C. and subsequent cured for 5 minutes at 150° C.

The fabrics are then tested according to DIN 53,906 (ignition time 6 seconds) for their flameproof character, according to ASTM D 1388-641 for their softness and according to ASTM D 1424-63 for their tear resistance. In addition the handle of the fabrics is assesed in accordance with the following scale.

0: unchanged
1: slight, stiffer than 0
2: somewhat stiffer than 0
3: stiff
4: very stiff The results are summarised in the following Table 6.

Table 6

| | PES/CO 67:33 treated with liquor | | PES/CO 50:50 treated with liquor | | CO treated with liquor | | PES/CO 67:33 untreated | PES/CO 67:33 untreated | CO untreated |
|---|---|---|---|---|---|---|---|---|---|
| | A | B | A | B | C | D | | | |
| Constituents of the liquors, g/l | | | | | | | | | |
| Product according to Example 20 (P-content:10.9 %) | 785 | — | 785 | — | 428 | — | | | |
| Product according to Example 21 (P-content: 9.0%) | — | 950 | — | 950 | — | 518 | | | |
| Condensation product from 1 mol of p-tert.-nonylphenyl and 9 mol of ethylene-oxide | 2 | 2 | 2 | 2 | 2 | 2 | | | |
| Di-Trimethylolmelamine | 103 | 103 | 103 | 103 | 113 | 113 | | | |
| Formaldehyde-melamine adduct modified with a fatty acid | — | — | — | — | 35 | 35 | | | |
| Silicon oil emulsion (40 %) | 35 | 35 | 35 | 35 | — | — | | | |
| pH of the liquor (adjusted with NaOH) | 5.6 | 5.6 | 5.6 | 5.6 | 5.5 | 5.5 | | | |
| Liquor up take % | 70 | 70 | 70 | 70 | 70 | 70 | | | |
| g phosphorus / kg of fabrics | 60 | 60 | 60 | 60 | 35 | 35 | | | |
| Flameproof character | | | | | | | | | |
| Burning time in seconds | 6 | 6 | 1 | 1 | 0 | 0 | | | |
| | | | | | | | burns | burns | burns |
| Char length in cm | 13.5 | 15 | 11 | 12.5 | 11 | | | | |
| Mechanical properties | | | | | | | | | |
| Handle | 2¼ | 2½ | 1¾ | 2½ | 0 | 0 | 0 | 0 | 0 |
| Tear resistance, warp, g | 2200 | 1970 | 1370 | 1400 | 616 | 1170 | 1980 | 1280 | 1080 |
| Stiffness, warp, mg/cm | 347 | 756 | 434 | 821 | 255 | 217 | 238 | 466 | 501 |

EXAMPLE 29

Fabrics of CO, PES/CO 67:33 and PES/CO 50:50 are padded with the liquors according to the following Table 7, dried at 80° to 100° C. and subsequently cured for 5 minutes at 150° C.

The fabrics are then washed and tested for their flameproof character as indicated in Example 23.

Untreated fabrics burn away.

The results are summarised in the following Table 7.

Table 7

|  | PES/CO 67:33 treated with liquor A | PES/CO 50:50 treated with liquor A | CO treated with liquor B |
|---|---|---|---|
| Constituents of the liquors 3/1 | | | |
| Product according to Example 22 (P-content: 14.5 %) | 590 | 590 | 322 |
| Condensation product from 1 mol of p-tert.-honylphenol and 9 mol of ethylene-oxide | 2 | 2 | 2 |
| Di-Trimethylolmelamine | 103 | 103 | 113 |
| Formaldehyde-alamine adduct modified with a fatty acid | — | — | 35 |
| Silicon oil emulsion (40 %) | 35 | 35 | — |
| pH of the liquor (adjusted with NaOH) | 5.5 | 5.5 | 5.5 |
| Liquor up take % | 70 | 70 | 70 |
| g Phosphorus / kg of fabrics | 60 | 60 | 35 |
| Degree of fixing | 74 | 76 | 67 |
| Flameproof character | | | |
| BT - Burning time in sec. | | | |
| CL - Char length in cm | | | |
| - after rinsing BT | 2 | 0 | 0 |
| CL | 10.5 | 10 | 9 |
| - after 20 washes BT | 4 | 1 | 0 |
| CL | 8.5 | 8.5 | 9.5 |
| - after 40 washes BT | 5 | 1 | 0 |
| CL | 15 | 9.5 | 9.5 |

What we claim is:

1. A water-soluble condensation product of hydroxymethylphosphonium compounds and amines which is produced by a process, comprising the essential step of condensing at 100° to 150° C. 1 mol of a tetrakis-(hydroxymethyl)phosphonium compound and 0.02 to 0.3 mol of an aliphatic primary monoamine with at most 8 carbon atoms or 0.02 to 0.1 mol of an aliphatic primary monoamine with 9 to 18 carbon atoms.

2. A product of claim 1, in which 0.1 to 0.3 mol of a primary alkyl-, hydroxyalkyl- or hydroxyalkoxyalkyl- or alkenyl amine with at most 8 carbon atoms is used.

3. A product of claim 1, in which 0.02 to 0.1 mol of a primary alkyl amine with 9 to 18 carbon atoms is used.

4. A product of claim 1, in which 0.1 to 0.3 mol of ethyl-, tertiaryoctyl-, monoethanol-, diglykol- or allylamine is used.

5. A product of claim 1, in which 0.1 to 0.25 mol of ethyl-, tertiaryoctyl-, monoethanol-, diglykol- or allylamine is used.

6. A product of claim 1, in which 0.02 to 0.1 mol of dodecyl- or stearylamine is used.

7. A product of claim 1, in which a tetrakis-(hydroxymethyl)-phosphonium salt or tetrakis-(hydroxymethyl)-phosphonium hydroxide is used.

8. A product of claim 1, in which a tetrakis-(hydroxymethyl)-phosphonium salt is used.

9. A product of claim 1, in which a tetrakis-(hydroxymethyl)-phosphonium halide is used.

10. A product of claim 1, in which a tetrakis-(hydroxymethyl)-phosphonium chloride is used.

11. A product of claim 1, in which the condensation step is carried out at 110° to 140° C.

12. A product of claim 1, in which the condensation step is carried out in the presence of an aromatic hydrocarbon as inert solvent.

13. A product of claim 1, in which xylene is used as inert solvent.

14. A product of claim 1, in which after the condensation step free hydroxy groups of the condensation products are etherified with an alkanol with 1 to 4 carbon atoms.

15. A product of claim 1, in which after the condensation step the salts of the condensation products are converted into the corresponding hydroxides.

* * * * *

UNITED STATES PATENT AND TRADEMARK OFFICE
CERTIFICATE OF CORRECTION

PATENT NO. : 4,185,037

DATED : January 22, 1980

INVENTOR(S) : Herman Nachbur, et al

It is certified that error appears in the above-identified patent and that said Letters Patent is hereby corrected as shown below:

On the title page the following should be added:

-- [30] Foreign Application Priority Data

Sept. 10, 1971 [CH] Switzerland.....13309/71 --.

Signed and Sealed this

Fourteenth Day of May 1985

[SEAL]

Attest:

DONALD J. QUIGG

Attesting Officer     Acting Commissioner of Patents and Trademarks